United States Patent
Tschritter

(10) Patent No.: US 10,458,964 B2
(45) Date of Patent: Oct. 29, 2019

(54) METHOD FOR RAPIDLY DETERMINING SULFUR CONTENT IN A PLURALITY OF SAMPLES

(71) Applicant: E I DU PONT DE NEMOURS AND COMPANY, Wilmington, DE (US)

(72) Inventor: Jonathan Samuel Tschritter, Chesterfield, VA (US)

(73) Assignee: DUPONT SAFETY & CONSTRUCTION INC., Wilmington, DE (US)

( * ) Notice: Subject to any disclaimer, the term of this patent is extended or adjusted under 35 U.S.C. 154(b) by 19 days.

(21) Appl. No.: 15/720,669

(22) Filed: Sep. 29, 2017

(65) Prior Publication Data

US 2019/0101514 A1    Apr. 4, 2019

(51) Int. Cl.

| G01N 31/12 | (2006.01) |
|---|---|
| C01B 17/96 | (2006.01) |
| D01F 6/60 | (2006.01) |
| G01J 3/30 | (2006.01) |
| G01N 21/73 | (2006.01) |
| G01N 33/44 | (2006.01) |
| G01J 3/00 | (2006.01) |

(52) U.S. Cl.
CPC ............ *G01N 31/12* (2013.01); *C01B 17/96* (2013.01); *D01F 6/605* (2013.01); *G01J 3/30* (2013.01); *G01N 21/73* (2013.01); *G01N 33/44* (2013.01)

(58) Field of Classification Search
CPC ........ G01N 31/12; G01N 31/00; C01B 17/96; G01J 3/30; G01J 3/28; G01J 3/00
USPC .......................................................... 436/119
See application file for complete search history.

(56) References Cited

U.S. PATENT DOCUMENTS

| 9,086,382 | B2 | 7/2015 | Tschritter | |
|---|---|---|---|---|
| 2013/0014329 | A1 | 1/2013 | Knoff et al. | |
| 2013/0224873 | A1* | 8/2013 | Fallis | C07D 257/04 436/119 |
| 2014/0356611 | A1 | 12/2014 | Allen et al. | |

OTHER PUBLICATIONS

PCT International Search Report, dated Nov. 28, 2018, for International Application No. PCT/US2018/053029, filed Sep. 27, 2018; ISA/EPO; Eric Duijs Authorized Officer.

* cited by examiner

*Primary Examiner* — Christine T Mui

(57) ABSTRACT

Methods for measuring the sulfur content in a plurality of individual sulfur-containing fiber or article samples, comprising: a) contacting a plurality of samples with a solution comprising potassium hydroxide to convert the sulfur to potassium sulfate; b) concurrently and individually combusting the plurality of samples from step a) in a furnace at a temperature of greater than 650° C. to remove essentially all organic materials to produce a plurality of residues; c) dissolving each of the pluralities of residue in concentrated nitric acid to form individual residue solutions; and d) analyzing the individual residue solutions with Inductively Coupled Plasma (ICP) Emission Spectrometry to determine the sulfur content of each sample.

4 Claims, No Drawings

METHOD FOR RAPIDLY DETERMINING SULFUR CONTENT IN A PLURALITY OF SAMPLES

BACKGROUND OF THE INVENTION

Field of the Invention

The invention concerns methods of determining sulfur content in articles, for example, organic fibers and polymer resins.

Description of Related Art

High-performance polymeric fibers and other articles can be made from high-performance polymers and copolymers by forming a suitable polymeric solution of polymer in a solvent, followed by, in the case of fibers, spinning the polymer solution into dope filaments, removing solvent from the dope filaments, and washing and drying the fibers. If desired, the fibers can be further heat treated to tailor mechanical properties. Alternatively, other articles such as films, etc., can be made from such polymeric solutions.

Sulfuric acid is a common solvent for forming such polymeric solutions. The use of the sulfuric acid solvent, however, can result in residual amounts of sulfur being left in the processed fibers or articles, either in the form of undesirable sulfur-containing impurities trapped in the polymer structure or sulfur bound to the polymer chain. In some instances, it is desirable to control the amount of residual amount of sulfur in the fibers or articles, and therefore accurate methods for determining sulfur content in fiber and article samples are desirable. An accurate determination of sulfur content in such samples can be difficult.

U.S. Pat. No. 9,086,382 to Tschritter discloses methods for measuring the sulfur content in a fiber or polymer resin sample by contacting the sample with a solution comprising sodium hydroxide to convert the sulfur to sodium sulfate, followed by combusting the sample to remove essentially all organic materials and produce a residue. The residue is further dissolved in concentrated nitric acid and the sulfur content of the sample is determined using ICP Emission Spectrometry.

However, it is desirable to have an even more rapid process for determining sulfur content; and a process that can address simultaneous testing of a number of samples. This is highly desirable in a manufacturing situation wherein fibers are being made on a continuous basis and quick determination of residual sulfur values are desired.

SUMMARY OF THE INVENTION

This invention relates to method of measuring the sulfur content in a plurality of individual sulfur-containing fiber or article samples, the method comprising the steps of:

a) contacting a plurality of sulfur-containing fiber or article samples with an aqueous solution comprising potassium hydroxide to convert the sulfur to potassium sulfate;

b) concurrently and individually combusting the plurality of samples from step a) in a furnace at a temperature of greater than 650° C. to remove essentially all organic materials and produce a plurality of residues;

c) dissolving each of the pluralities of residue in concentrated nitric acid to form individual residue solutions; and d) analyzing the individual residue solutions with Inductively Coupled Plasma (ICP) Emission Spectrometry to determine the sulfur content of each sample.

DETAILED DESCRIPTION OF THE INVENTION

This invention relates to methods for measuring the sulfur content in a plurality of individual sulfur-containing fiber or article samples, the methods including a step of contacting a plurality of the sulfur-containing fiber or article samples with an aqueous solution comprising potassium hydroxide to convert the sulfur to potassium sulfate.

U.S. Pat. No. 9,086,382 to Tschritter discloses a method for measuring the sulfur content in a fiber or polymer resin sample by contacting the sample with a solution comprising sodium hydroxide to convert the sulfur to sodium sulfate. The sample is then combusted in a furnace to remove essentially all organic materials and produce a residue that is further analyzed to determine the sulfur content of the sample. Tschritter further discloses that the furnace temperature for a testing a single sample can be set to a temperature of 400-800° C., with the time for complete ashing of the sample requiring 2 to 10 hours. Tschritter exemplifies that just the step of ashing a sample with furnace temperature of 600° C. can take 5 hours.

It has been found that it takes considerably longer times to ash a plurality of samples in a furnace at one time. There is obviously more sample mass that must be combusted, and with that more mass, there are more containers for the samples or some larger type of holder for the samples that keeps each of the plurality of samples separate. It is believed that simply raising the temperature of the furnace to increase the driving force is not a viable option, in that there is a concern that some of the sulfate salt could be evolved from the combusting sample, meaning that some of the sulfate salt will be irretrievably lost, with the ultimate analysis on the ash providing a sulfur determination that is not accurate.

In particular, it has been found that if the furnace temperature is raised close to the melting point of the sulfate salt, accuracy can suffer. In addition to localized hot spots in the furnace potentially evolving some of the sulfate salt, if localized melting occurs, some of the sulfate salt can splatter out of the sample container. The melting point of sodium sulfate is 884° C., meaning that there is limited ability to increase the furnace temperature and speed up the ashing of the samples when sodium hydroxide is used to digest the sample, making sodium sulfate. On the other hand, the melting point of potassium sulfate is 1062° C., which provides a temperature cushion of about 200 additional degrees Celsius when potassium hydroxide rather than sodium hydroxide is used to digest the sample.

The inventive method includes contacting a plurality of sulfur-containing fiber or article samples with an aqueous solution comprising potassium hydroxide to convert the sulfur to potassium sulfate. The fiber or polymer resin samples can be placed in any suitable containers for treatment with the dilute base. Such containers should be ones that do not contaminate the samples or interfere with obtaining an accurate sulfur content measurement. One type of suitable container is a quartz crucible. A plurality of crucibles or containers are preferably used, each having a sample to be measured.

An amount of fiber or polymer resin suitable for producing a sample sufficient to be analyzed by ICP is then placed in each container. In some embodiments, 0.3 to 0.6 grams of sample is used for each container. This method is especially useful for better precision measurement of the sulfur content of samples having a sulfur content of 1 weight percent or less, preferably 0.1 weight percent or less, and especially for samples having a sulfur content of 0.05 weight percent or less.

Dilute potassium hydroxide is added to each fiber sample in each container such that the sample is preferably covered with the aqueous solution. In some embodiments, each sample is covered with a minimum amount of solution so as minimize the liquid that must be evaporated in a further step. Any solution concentration that converts substantially all of the sulfur content of the sample to potassium sulfate may be utilized. In some embodiments, a 0.01 to 1 N potassium hydroxide solution is utilized. One preferred embodiment uses 0.1 N to 0.5 N potassium hydroxide solution. The samples are immersed in the potassium hydroxide solution for a time sufficient to convert the sulfur content in the fiber sample to potassium sulfate; this time is preferably 15 minutes or greater. While not wanting to be bound by theory, it is believed the treatment of the samples with base in this manner inhibits the volatilization and loss of sulfur during ashing.

The inventive method then further involves concurrently and individually combusting the plurality of samples in a furnace at a temperature of greater than 650° C. to remove essentially all organic materials and produce a plurality of residues. The containers comprising the fiber or polymer resin sample and the dilute base solution can first be heated at low or moderate temperatures (about 100-200° C.) until a substantial portion of the water in the aqueous caustic solution is evaporated. Preferably, substantially all of the liquid (water) is evaporated. A hot plate or other heat source may be used for the evaporation. In a preferred embodiment, the liquid is slowly evaporated. In some preferred embodiments, a time of 10 minutes to one hour is required. In one embodiment, evaporation takes about 30 minutes or less, with a range of about 20 to about 40 minutes being typical.

The dried fiber or polymer resin samples are then ashed, concurrently and individually combusting the plurality of samples. Any suitable method of combustion may be utilized for the ashing. In some embodiments, a muffle furnace, such as a THERMOLYNE™ 62770 furnace may be utilized. The furnace is preferably set to a temperature of greater than 650 degrees Celsius. In one embodiment, a temperature of up to about 900 degrees C. is used, with the overall preferred furnace temperature range being 700 to 800° C., nominally about 750° C. The ashing should occur for a time to allow substantially complete ashing of all the samples. In some embodiments, this time is less than 2 hours; in some preferred embodiments, this time is one hour or less.

The inventive method continues by dissolving each of the pluralities of residue in concentrated nitric acid to form individual residue solutions. Specifically, after ashing, the resulting samples are individually contacted with concentrated nitric acid (preferably commercial grade) and the resulting mixture is then diluted with purified water (such as MILLI-Q® water) to produce a sample suitable for ICP analysis. In some embodiments, a ratio of 20:1 to 5:1 water to acid is used. In one preferred embodiment, 2 grams of nitric acid and 25 grams of water are used.

The inventive method then involves analyzing the individual residue solutions with Inductively Coupled Plasma (ICP) Emission Spectrometry to determine the sulfur content of each sample. Specifically, the resulting solution for each sample to be tested can then be transferred from the container to a centrifuge tube and then analyzed in the axial mode by ICP Emission Spectrometer. The results are calibrated using a blank, such as a 10 ppm Sulfur Standard, and a 100 ppm Sulfur standard. Such standards may be obtained from High Purity Standards located in Charleston, S.C.

Inductively Coupled Plasma (ICP) Emission Spectrometry is well known in the art as a tool for detection and quantification of trace metals in a sample. The method utilizes inductively coupled plasma that produces excited atoms and ions. These excited atoms and ions emit electromagnetic radiation at wavelengths that are characteristic for a particular element. Based on the intensity of the emission, the concentration of the element within the sample can be determined by comparison with samples of known concentration. One suitable instrument for performing this analysis is the Perkin Elmer 5400 DV ICP Emission Spectrometer.

EXAMPLES

Representative Method of Determining Sulfur Content

A clean 100-mL Quartz crucible is placed on a 4-decimal place analytical balance and the balance is zeroed. Between 0.3 g-0.6 g of fiber or polymer resin is weighed into the crucible. Small amounts potassium hydroxide of suitable concentration are carefully added to the fiber or polymer resin sample until it is covered with the solution. This is repeated for all the samples to be measured. The plurality of samples is then allowed to set in the solution for 15 minutes. The plurality of samples is heated on a hotplate at a temperature of 190 deg C. and the liquid from the solution is allowed to slowly evaporate. This step usually takes about 30 minutes. After the solution has completely evaporated in all the 100-mL crucibles, the plurality of crucibles is placed in a muffle furnace set at the desired combusting temperature. The samples are allowed to ash, and afterward the plurality of crucibles is removed from the muffle furnace and allowed to cool for about 30 minutes. For each sample, 2 milli-liters (mL) of concentrated environmental grade nitric acid is added to the 25-mL graduated cylinder and the cylinder is then filled to the 25 mL mark with MILLI-Q® water. The acid solution is transferred from the 25-mL graduated cylinder to each 100-mL crucible containing the ashed material. As soon as the acid solution is added, the ash immediately dissolves. The solution from each crucible is then transferred from the 100-mL crucible to a 15-mL plastic centrifuge tube. Each acid solution is then analyzed separately in the axial mode by a Perkin Elmer 5400 DV ICP Emission Spectrometer using the 181.975 nm Sulfur Emission line. The ICP Emission Spectrometer is calibrated using a blank, a 10 ppm Sulfur Standard, and a 100 ppm Sulfur standard. The ICP standards were prepared by High Purity Standards located in Charleston, S.C.

Example 1

Fiber samples comprising fibers made from a polymer derived from the copolymerization of 5(6)-amino-2-(p-aminophenyl)benzimidazole (DAPBI), para-phenylenediamine (PPD) and terephthaloyl dichloride (TCI) and spun from sulfuric acid solution were concurrently and individually prepared per the representative test method. Two fiber samples were digested using 0.5N potassium hydroxide, followed by combusting at 700° C. for one hour. The samples had a sulfur content of 0.4207% and 0.4029%, respectively, for an average sulfur concentration of 0.412%.

This result agreed with the sulfur concentration measurement of identical fiber samples used as a control, which were also digested using 0.5N potassium hydroxide but are combusted at 600° C. for five hours. These control samples had an average sulfur concentration of 0.415%.

Example 2

Fiber samples comprising fibers made from poly(p-phenylene terephthalamide) polymer spun from sulfuric acid solution were concurrently and individually prepared and tested per the representative test method. Two fiber samples were digested using 0.1N sodium hydroxide (NaOH), followed by combusting at 900° C. for 30 minutes. The NaOH-digested samples were determined to have an average sulfur content of 1080 ppm.

Two more fiber samples, identical to the NaOH-digested samples, were then digested using 0.1N potassium hydroxide (KOH) followed by combusting at 900° C. for 30 minutes. The KOH-digested samples were determined to have an average sulfur content of 1860 ppm.

The samples digested with KOH agreed well with control samples digested with 0.1N NaOH and combusted at 600° C. for five hours, which were found to have an average sulfur concentration of 2060 ppm. The faster, higher-temperature KOH process provided a sulfur concentration measurement that was within about 10% of the control samples (using the slower, lower-temperature NaOH process), which was deemed acceptable experimental error. The faster, higher-temperature process using NaOH-digested samples provided a sulfur concentration measurement that was unacceptable in that it varied from the control by almost 48%.

Example 3

This example further illustrates the impact of temperature on the measurement of sulfur. As a control, the amount of sulfur in a sulfuric acid-spun poly(p-phenylene terephthalamide) fiber sample was determined using the representative method to be 1530 ppm by digesting in NaOH followed by ashing at 600° C. for 5 hours. The amount of sulfur in identical fiber samples was then determined via digestion in NaOH followed by ashing at two elevated temperatures for one hour. This was then repeated on two more identical fiber samples, with KOH as the digesting base, again ashing for one hour. The percent difference in sulfur concentration measured at elevated temperatures (and shorter times) versus the sulfur concentration measured at 600° C. (and longer time) was then calculated, and the results are shown in the Table.

The melting point of sodium sulfate (NaOH) is 884° C., while the melting point of potassium sulfate (KOH) is 1062° C. The table illustrates that as the combusting temperature moves close to the melting point of the particular sulfate, the measurement surprisingly becomes more variable, which is believed to confirm the assumption that elevated ashing temperatures near the melting point of the sulfate can result in sulfate loss, and subsequent inaccuracies in the concentration measurement.

TABLE

| Item | Combusting Temperature (° C.) | Absolute Percent Difference in Measured Sulfur from Control | |
|---|---|---|---|
| | | NaOH | KOH |
| 3-1 | 900 | 30 | 4 |
| 3-2 | 1000 | 63 | 66 |

What is claimed:

1. A method of measuring the sulfur content in a plurality of individual sulfur-containing fiber or article samples, the method comprising the steps of:
    a) contacting a plurality of sulfur-containing fiber or article samples with an aqueous solution comprising potassium hydroxide to convert the sulfur to potassium sulfate;
    b) concurrently and individually combusting the plurality of samples from step a) in a furnace at a temperature of greater than 650° C. to remove essentially all organic materials and produce a plurality of residues;
    c) dissolving each of the pluralities of residue in concentrated nitric acid to form individual residue solutions; and
    d) analyzing the individual residue solutions with Inductively Coupled Plasma (ICP) Emission Spectrometry to determine the sulfur content of each sample.

2. The method of claim 1, where said solution comprising potassium hydroxide is an aqueous solution having a potassium hydroxide content in the range of from 0.01 to 1 N.

3. The method of claim 1 wherein after step a) and prior to step b), the plurality of sulfur-containing samples of step a) are further heated to remove liquid from the samples.

4. The method of claim 2 wherein after step a) and prior to step b), the plurality of sulfur-containing samples of step a) are further heated to remove liquid from the samples.

* * * * *